(12) United States Patent  (10) Patent No.: US 8,801,760 B2
Amato et al.  (45) Date of Patent: Aug. 12, 2014

(54) GROWTH CONTROL DEVICE

(75) Inventors: Matthew F. Amato, Lawrenceville, NJ (US); Stephen B. Walulik, Stewartsville, NJ (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/483,231

(22) Filed: May 30, 2012

(65) Prior Publication Data

US 2012/0239040 A1 Sep. 20, 2012

Related U.S. Application Data

(63) Continuation of application No. 12/166,833, filed on Jul. 2, 2008, now Pat. No. 8,273,111.

(51) Int. Cl.
*A61B 17/80* (2006.01)

(52) U.S. Cl.
USPC .......................................... 606/280; 606/286

(58) Field of Classification Search
CPC ...................................................... A61B 17/80
See application file for complete search history.

(56) References Cited

U.S. PATENT DOCUMENTS

2004/0102777 A1* 5/2004 Huebner .......................... 606/69
2004/0158251 A1* 8/2004 Morrison et al. ............... 606/71

* cited by examiner

*Primary Examiner* — Nicholas Woodall
*Assistant Examiner* — Christine Nelson
(74) *Attorney, Agent, or Firm* — Harness, Dickey

(57) ABSTRACT

A growth control device includes a bone plate having a stepped profile defined by a first level, a second level and an intermediate ramp connecting the first and second levels. The first level includes a first threaded hole for receiving a first bone fastener and the second level includes a second threaded hole for receiving a second bone fastener. The bone plate includes a proximal pair of side female notches, a distal pair of side female notches, a proximal guide hole and a distal guide hole.

22 Claims, 16 Drawing Sheets

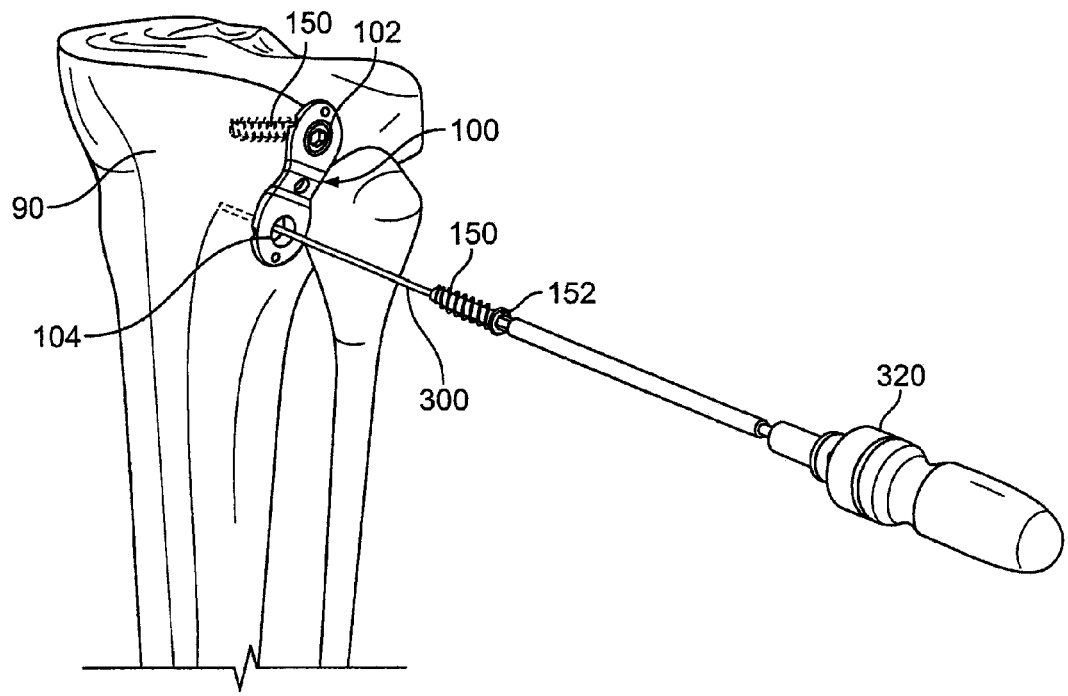
FIG. 18
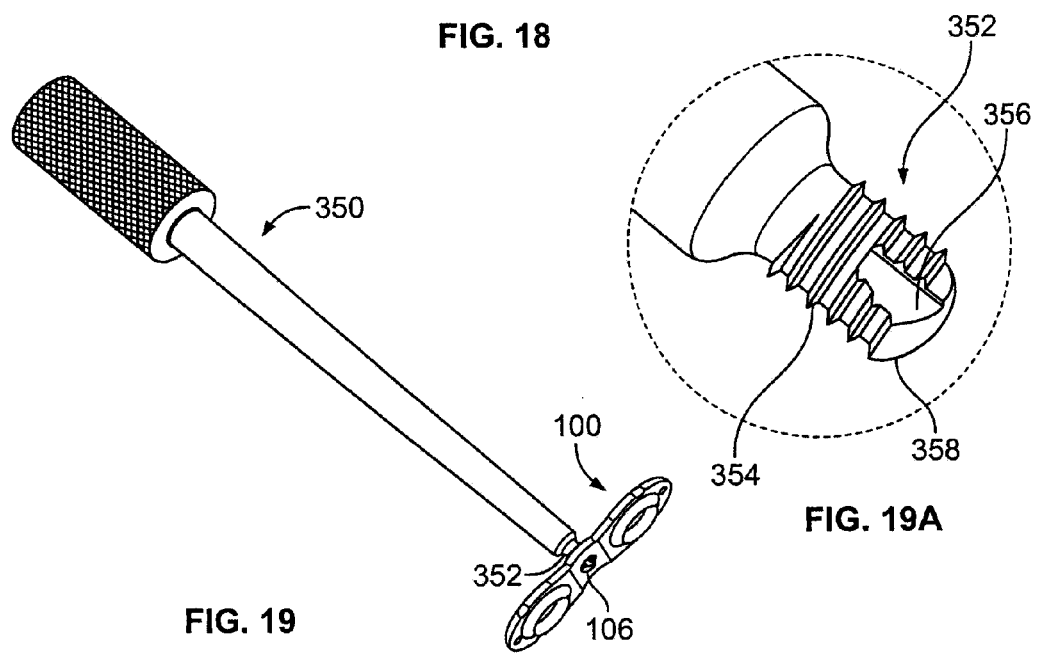
FIG. 19
FIG. 19A

GROWTH CONTROL DEVICE

Various devices are known for correcting bone deformities in pediatric or other patients.

The present teachings provide a growth control device that can be used for correcting bone deformities.

SUMMARY

The present teachings provide a growth control device. In one aspect the growth control device can include a bone plate having a stepped profile defined by a first level, a second level and an intermediate ramp connecting the first and second levels. The first level can include a first threaded hole for receiving a first bone fastener and the second level can include a second threaded hole for receiving a second bone fastener. The bone plate can include a proximal pair of side female notches, a distal pair of side female notches, a proximal guide hole and a distal guide hole.

In another aspect, the growth control device can include a bone plate as above, first and second bone fasteners receivable in the first and second holes and angulatable relative to an axis substantially orthogonal to the bone plate within a cone of angulation, and a holding device having first and second arms pivotable relative to one another, and first and second legs extending from the first and second arms. The first and second legs have first and second distal ends defining a curved split slot and a pair of male notches extending from a lower surface of the split notch, the first and second male notches engaging the first and second female notches when one of the proximal or distal ends of the bone plate is held in the curved split slot.

In a further aspect, the growth control device can include a plurality of bone plates of different sizes, each bone plate having first and second threaded holes and an intermediate portion between the first and second holes, the intermediate portion having a third threaded hole. The plurality of bone plates can include at least one stepped bone plate having an intermediated portion in the form of a ramp, and at least one arched bone plate having an intermediate portion in the form of a curved arch.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIGS. 10-18 are views illustrating various aspects of implanting a growth control device in the tibia with associated devices according to the present teachings;

FIG. 19 is a perspective view of a growth control device coupled to an extractor according to the present teachings; and FIG. 19A is an enlarged detail of a distal end of the extractor of FIG. 19.

DESCRIPTION OF VARIOUS ASPECTS

The following description is merely exemplary in nature and is in no way intended to limit the present teachings, applications, or uses. For example, although the present teachings are illustrated for procedures relating to femur and/or tibia, the present teachings can be used for any long bones in pediatric or other surgery. In particular, the present teaching can be used to correct angular deformities in long bones in pediatric patients.

Figure 1:
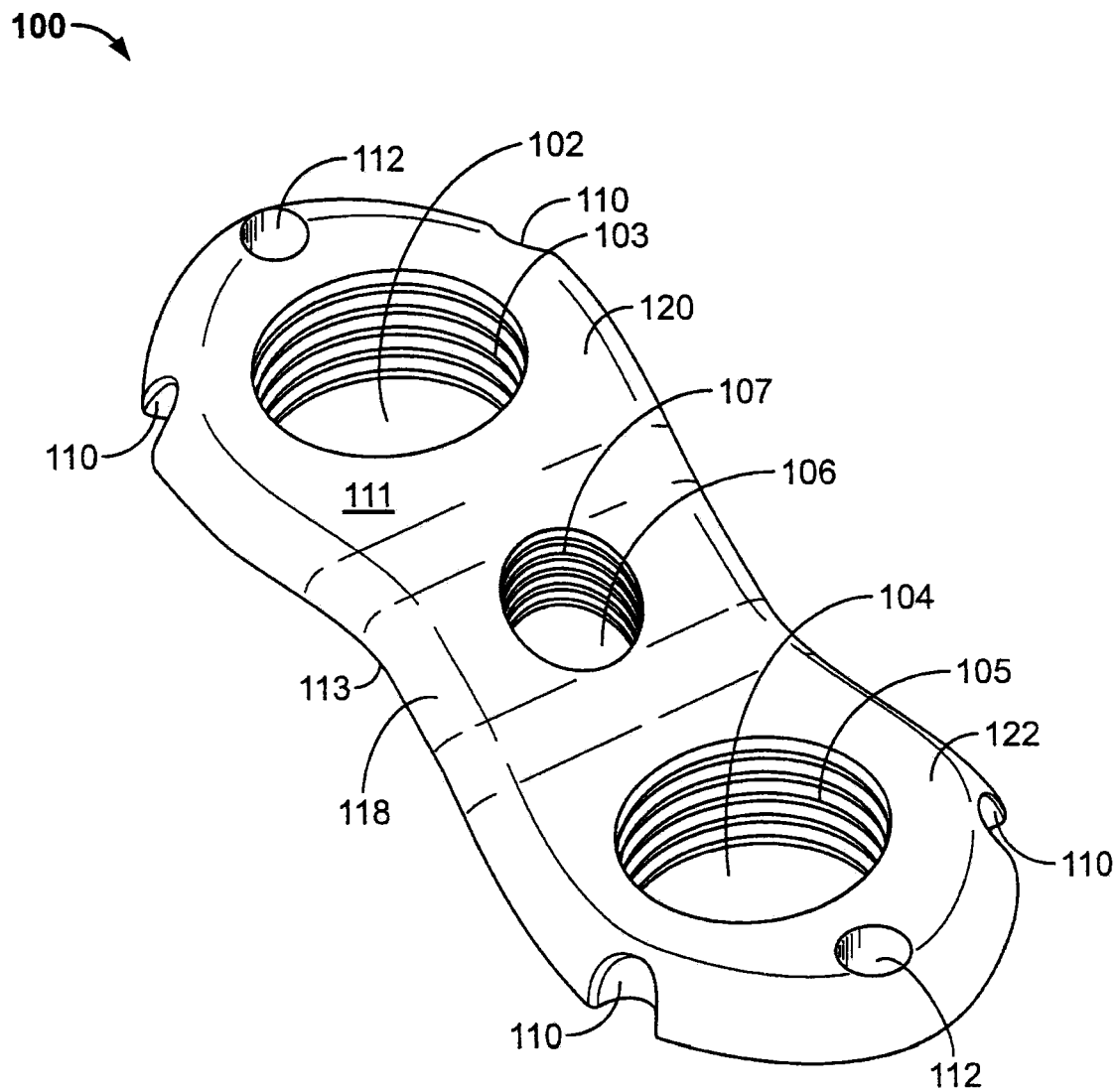
FIG. 1 is a perspective view of a growth control device according to the present teachings.
Figure 1A:
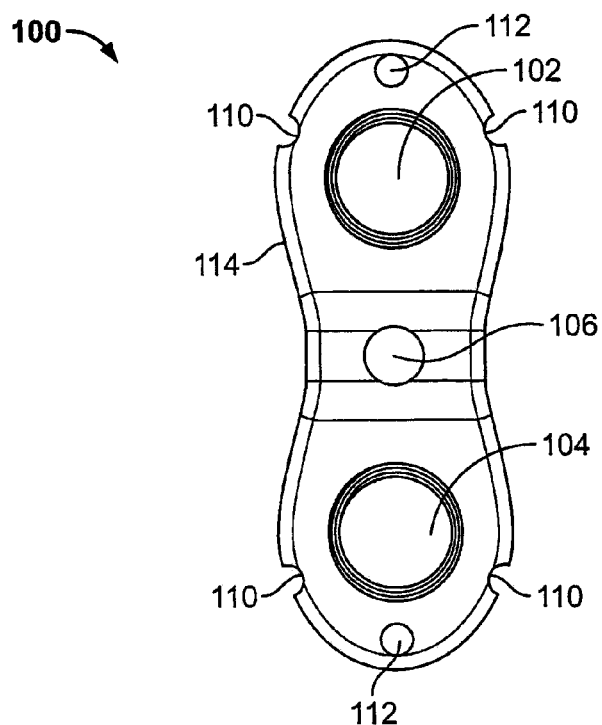
FIG. 1A is a top view of the growth control device of FIG. 1.
Figure 2:
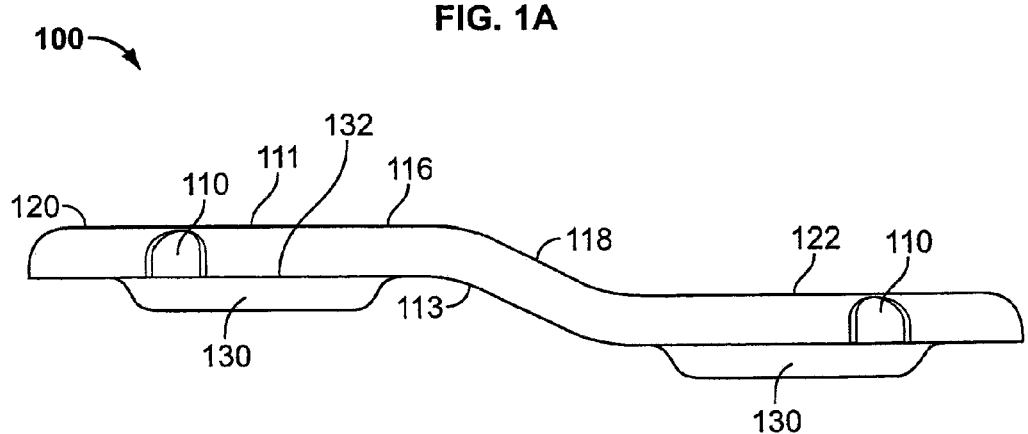
FIG. 2 is an elevated side view of the bone plane of FIG. 1.
Figure 3:
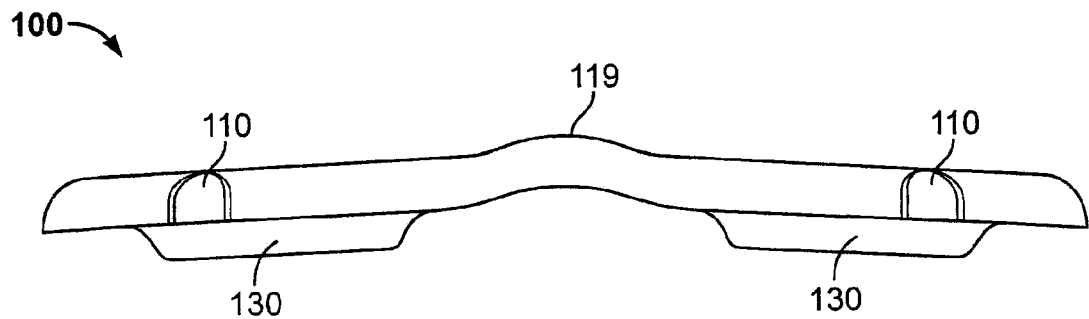
FIG. 3 is a perspective view of a growth control device according to the present teachings.
Figure 3A:
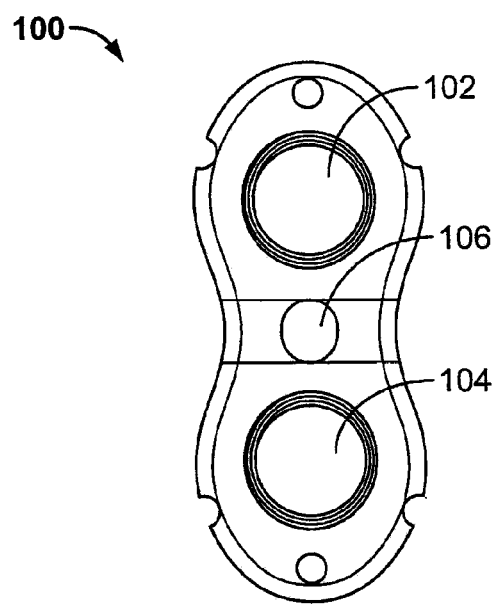
FIG. 3A is a top view of the growth control device of FIG. 3.
Figure 6:
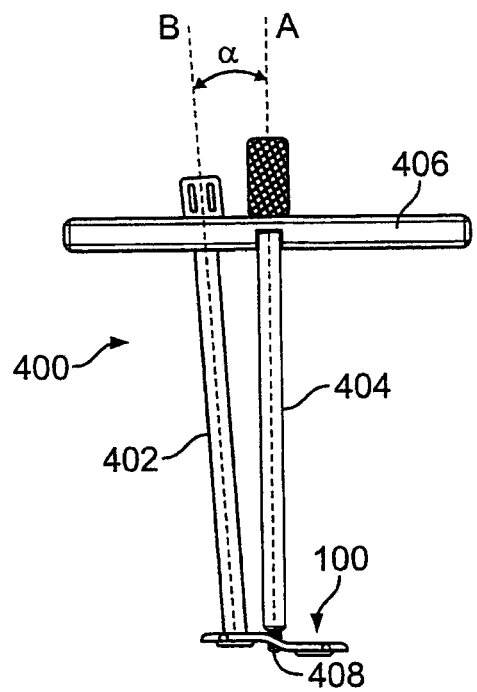
FIG. 6 is an elevated side view of the growth control device of FIG. 1 shown with a targeting device.
Figure 7:
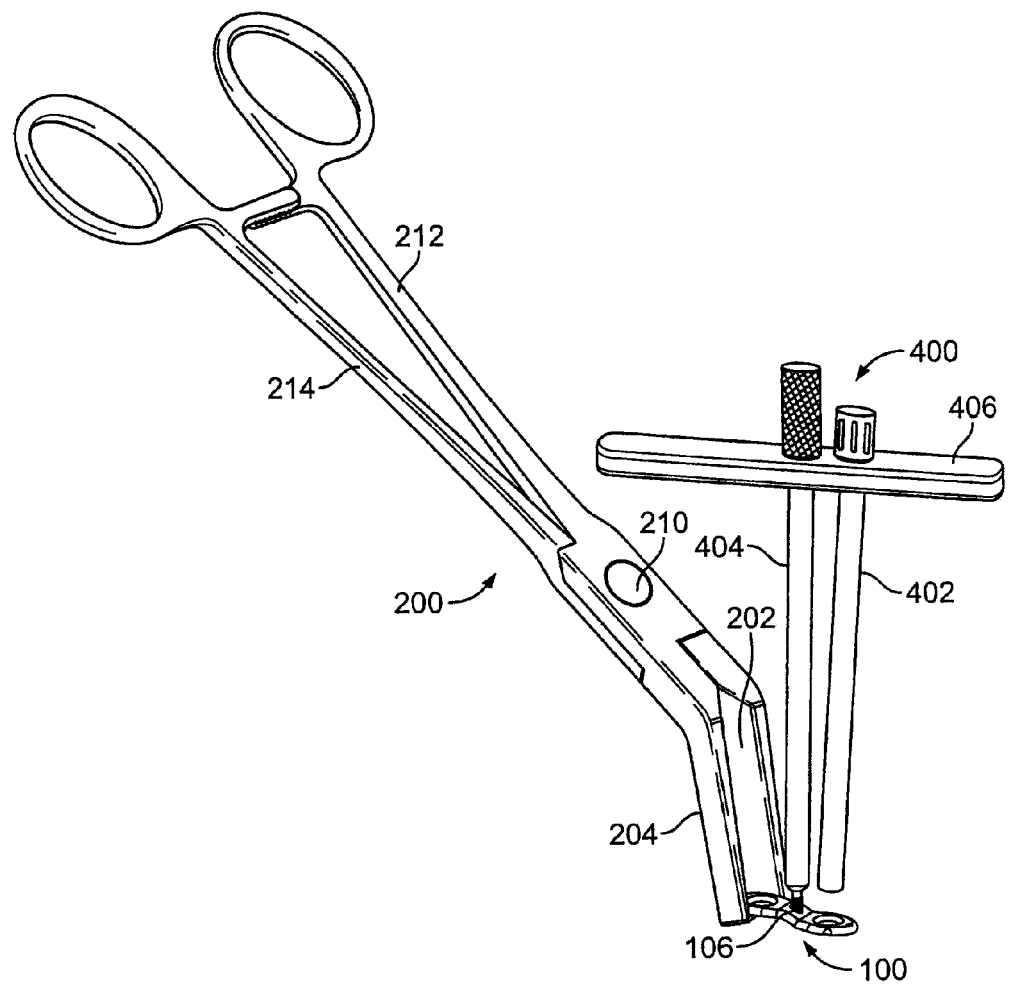
FIG. 7 is a perspective view of the growth control device of FIG. 1 shown with a holding and targeting devices.
Figure 8:
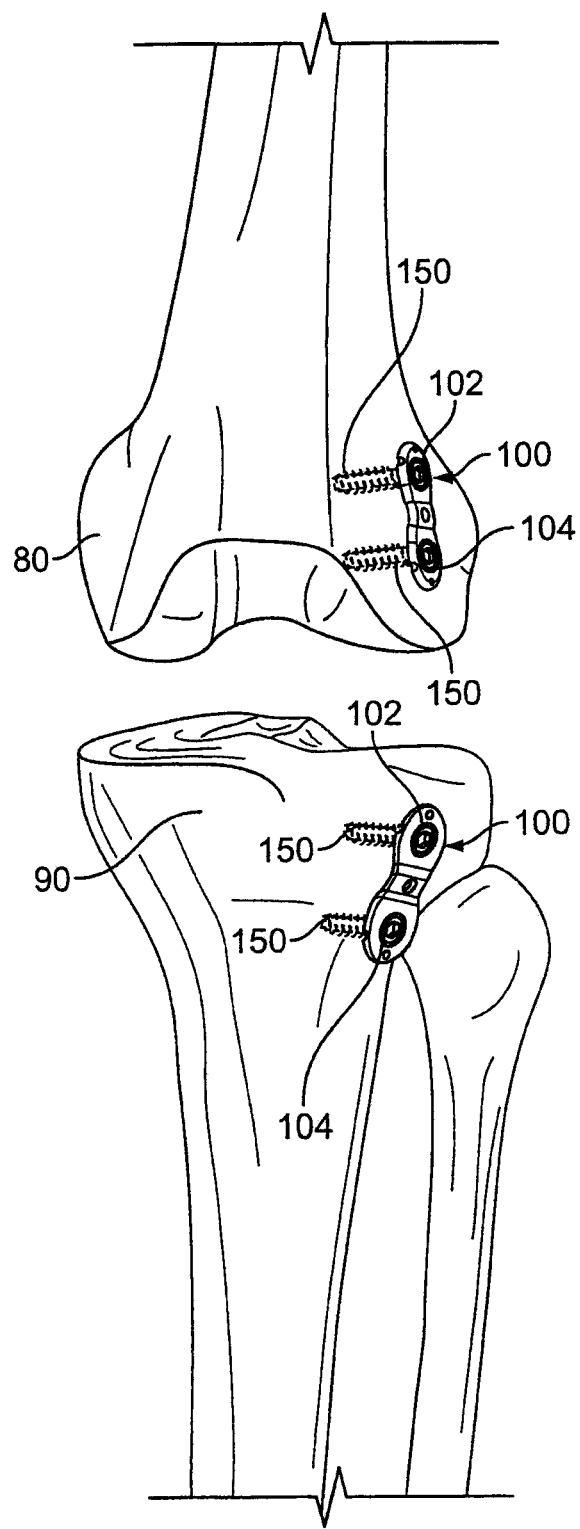
FIG. 8 is an environmental view showing a growth control device implanted in the femur and a growth control device implanted in the tibia according to the present teachings.

Referring to FIGS. 1-8, various aspects of exemplary growth control devices according to the present teachings is illustrated. The growth control device can include one or more bone plates 100. A bone plate 100 can have an anatomically contoured stepped or offset profile, as illustrated in FIGS. 1, 1A and 2, or an anatomically contoured humped or arched profile, as illustrated in FIGS. 3 and 3A. An environmental view of anatomically contoured bone plates 100, as implanted in the femur 80 and tibia 90 according to the present teachings, is illustrated in FIG. 8.

Figure 9:
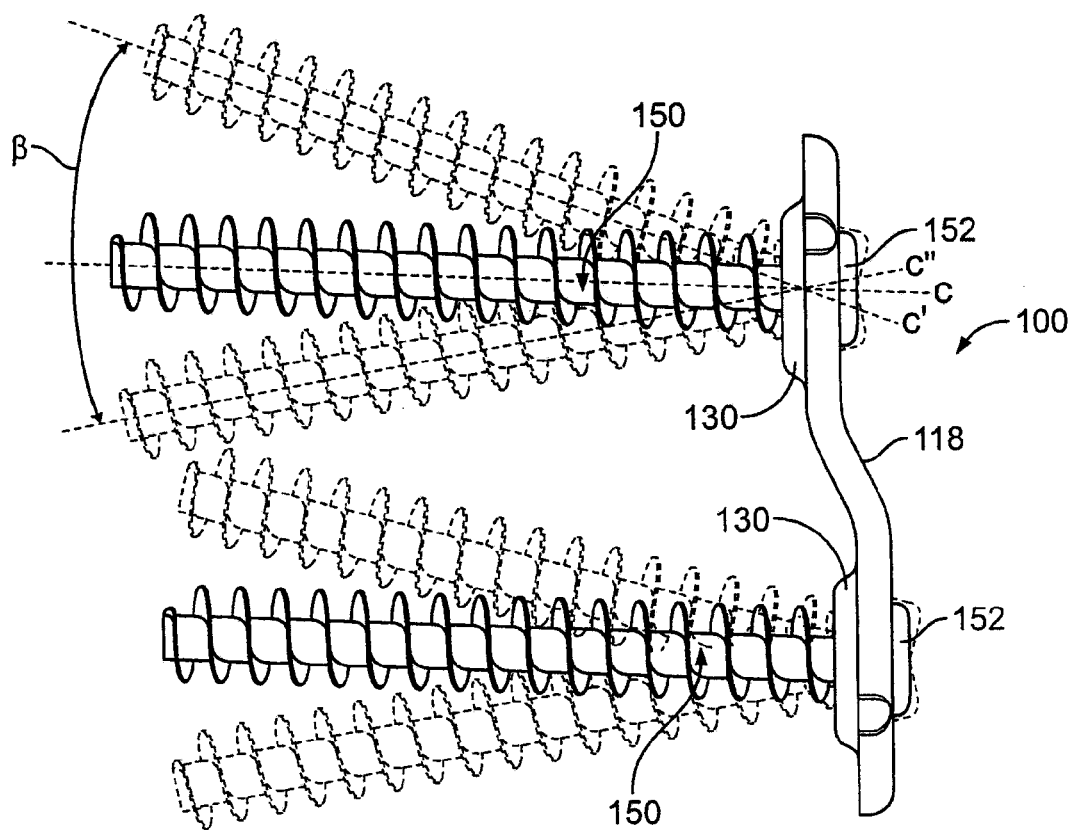
FIG. 9 is an elevated side view of the growth control device of FIG. 1 shown with variable-angle bone fasteners.

Generally, the growth control device can be used to provide gradual correction of an angular deformity in a long bone by restraining one side, medial or lateral, of the growing bone, causing the bone to grow on the opposite side, thereby forcing a natural correction by a non-symmetric corrective bone growth. Further, as illustrated in FIG. 8, the growth control device can include a bone plate 100 which is contoured and profiled for matching the anatomy of the particular bone, and non-locking threaded bone fasteners 150 that can angulate about an axis C perpendicular to the bone plate 100 within a cone of maximum angulation of an angle $\beta$ of about 32-degrees between axes C' and C'', as shown in FIG. 9. Each bone fastener 150 can be cannulated therethrough for receiving a guide wire 300, and can have a spherically shaped head 152 including a formation for engaging a driver 320, as shown in FIG. 18. The bone fasteners 150 can be low-profile cannulated titanium alloy screws with self-cutting tips and reverse buttress threads to guard against pull out.

More specifically, and referring to FIGS. 1, 1A and 2, the bone plate 100 can have, in a side elevated view, a stepped profile 116 that includes a first level 120, a second level 122 and an intermediate inclined or ramped portion 118 connecting the first level 120 to the second level, as shown in FIG. 2. The profile 116 can be shaped to conform to the anatomic contour of a long bone of a patient and can be provided in various sizes and shapes, including the relative dimensions of the first level 120, the second level 122 and the intermediate portion 118, to account for anatomic differences from bone to bone and from patient to patient, including patient's age, gender, and degree of deformity. The first level 120 and the second level 122 can be disposed in parallel and spaced apart planes.

Figure 4:
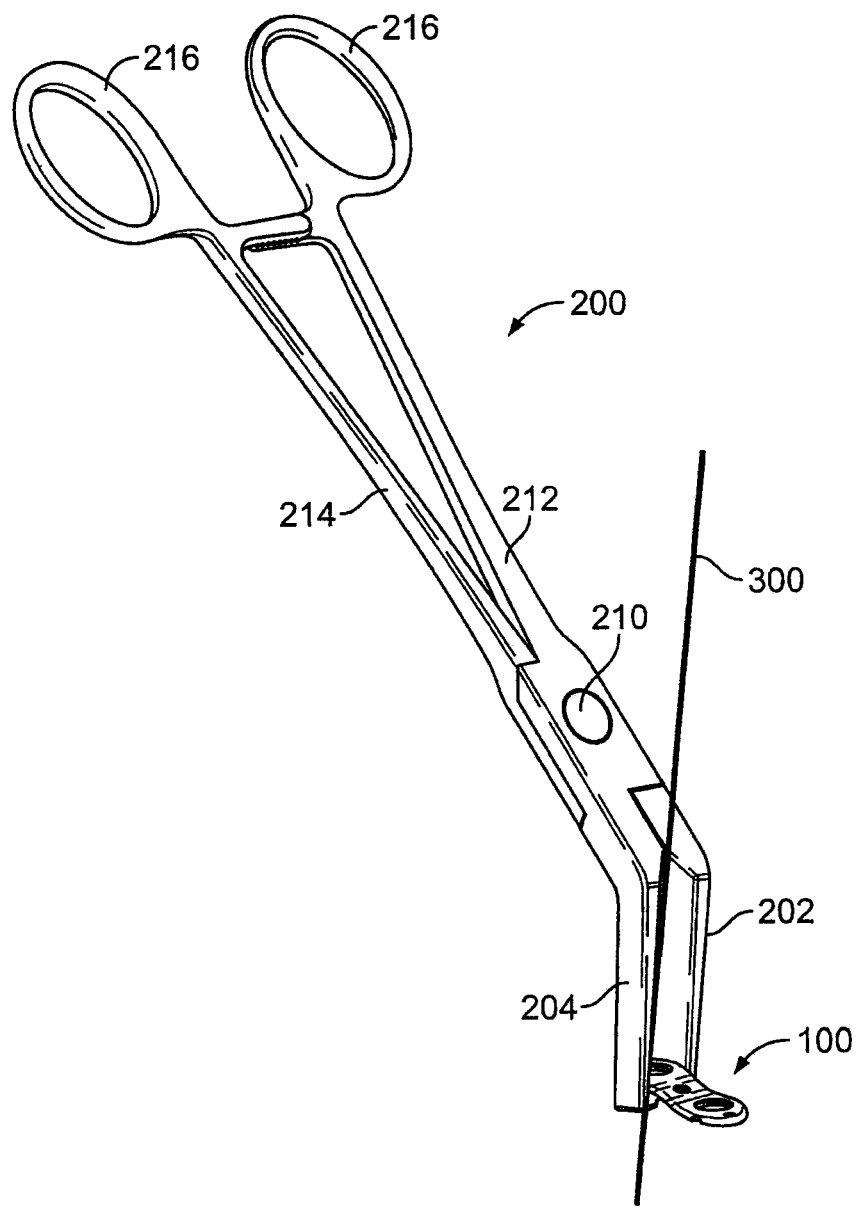
FIG. 4 is a perspective view of the growth control device of FIG. 1 shown with a holding device.
Figure 4A:
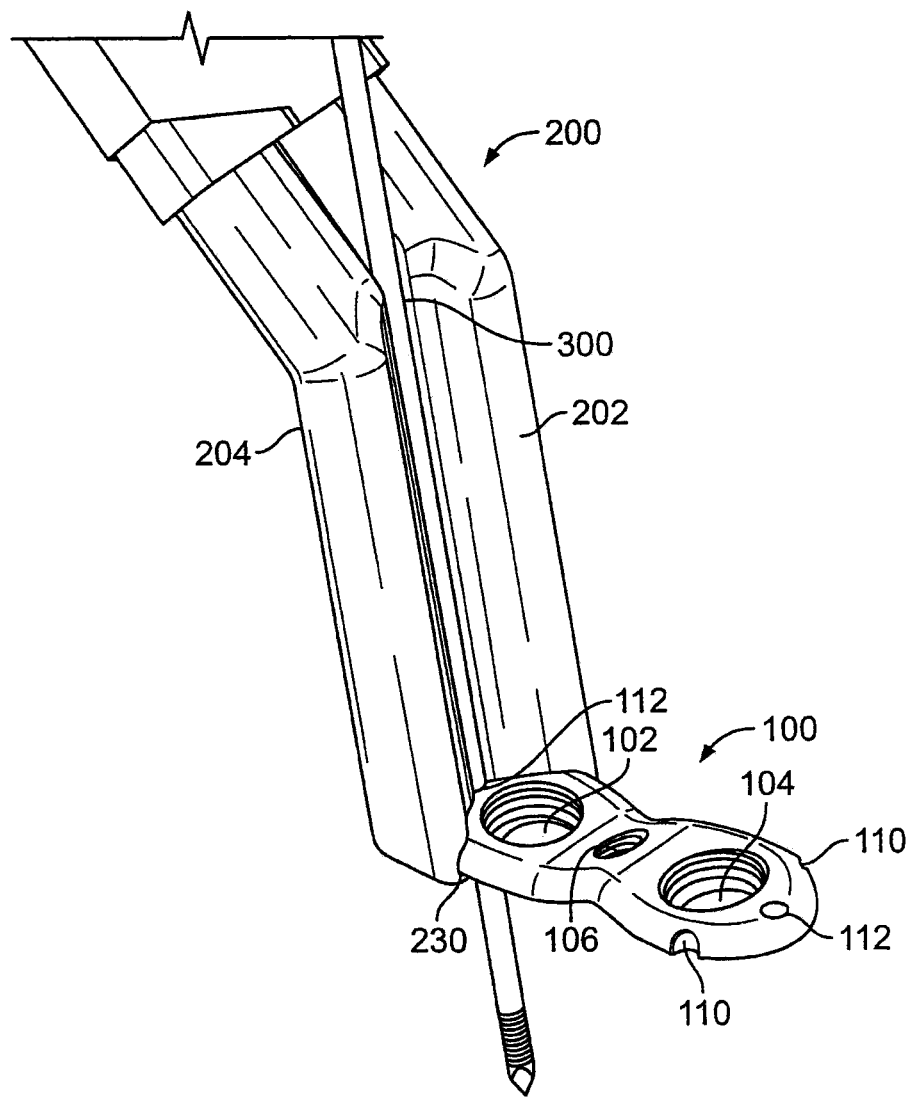
FIG. 4A is an enlarged detail of FIG. 4.
Figure 4B:
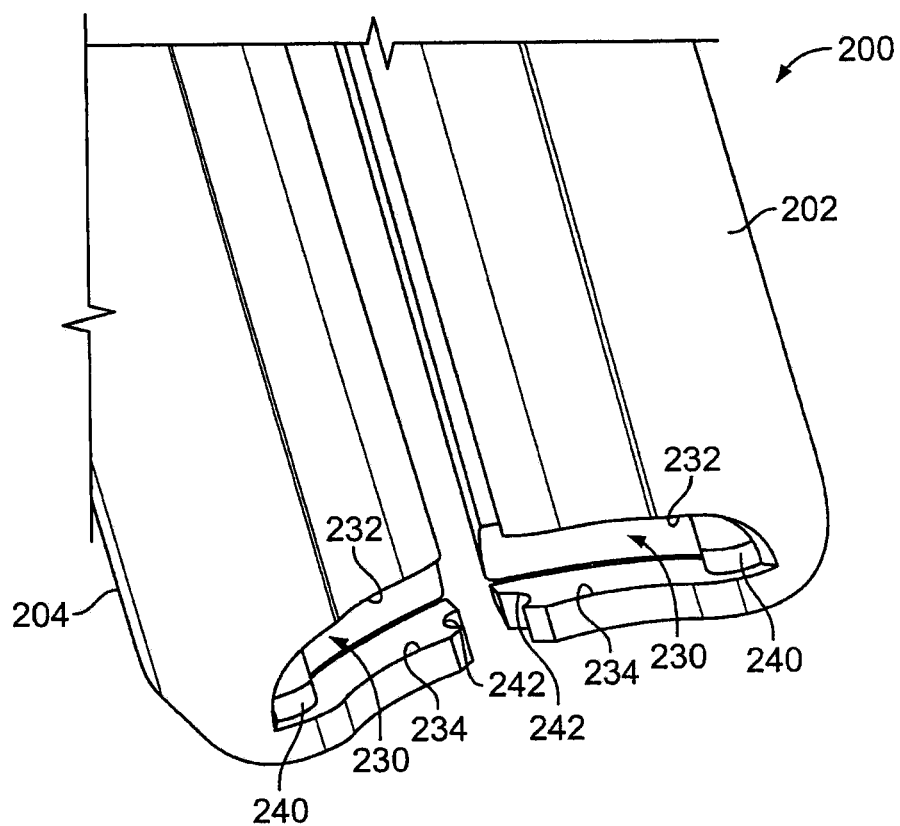
FIG. 4B is an enlarged detail of the holding device of FIG. 4.
Figure 5:
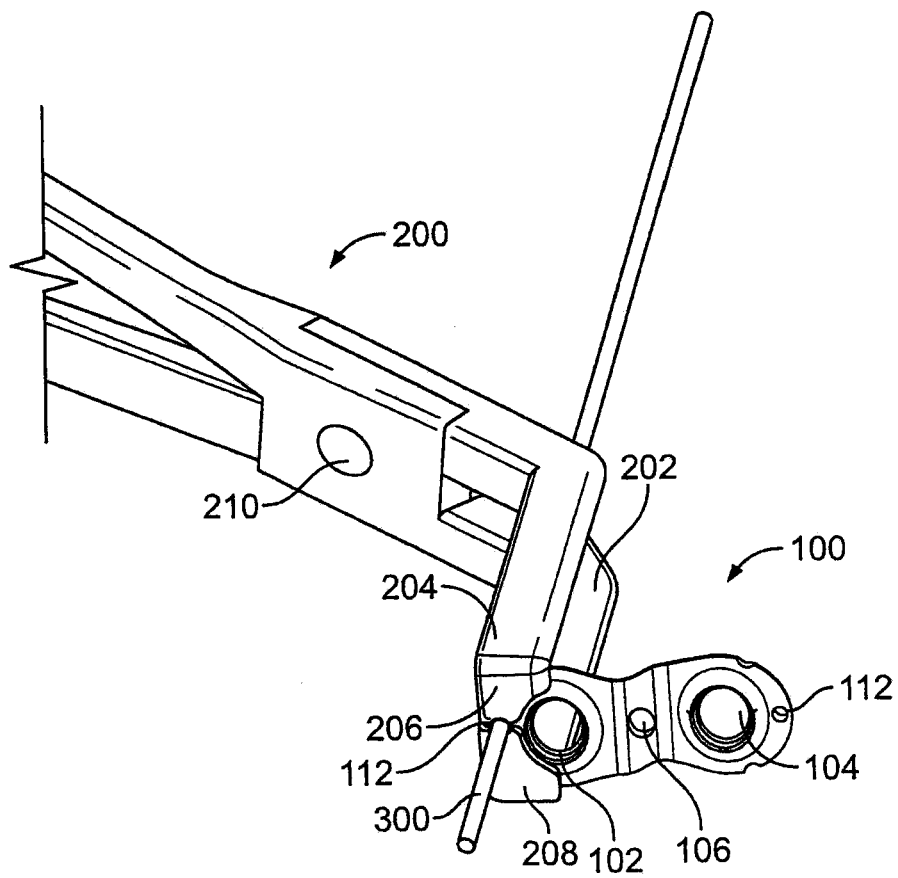
FIG. 5 is a perspective view of the growth control device of FIG. 1 shown with a holding device.

Referring to FIGS. 1-2, 4-7, 19, and 19A, the bone plate 100 can include first and second (proximal and distal) holes 102, 104 extending through the thickness of the bone plate 100 from an outward or upper surface 111 to an opposite bone-engaging surface 113. The holes 102, 104 define corresponding inner surfaces 103, 105, which are threaded and spherically shaped for receiving threaded fixation bone fasteners 150 having spherically shaped heads 152, as shown in FIG. 9. The bone plate 100 can also include a third or central hole 106, positioned between the first and second holes 102, 104. The third hole 106 can define a threaded inner surface 107 for engagement with a threaded distal end 408 of a post 400 of a targeting device and/or a threaded distal end 352 of an extractor 350, as shown in FIGS. 6, 7 and 19. Further, the bone plate 100 can include two smaller end openings or guide holes 112 at the proximal and distal ends of the bone plate 100 for guiding a K-wire or other guide wire 300 therethrough, as shown in FIG. 5, for example. The bone plate 100 can also include two pairs of female side notches 110, i.e., medial and lateral notches 110 at the proximal and distal ends of the bone plate 100, for engagement with forceps or other holding device 200, as shown in FIGS. 4, 4A, 4B, for example, and described below.

Referring to FIG. 2, the bone plate 100 can include first and second washers 130 surrounding the first and second holes 102, 104 on the bone engaging surface 113 of the bone plate 100. Each washer 130 can be unitarily integrated and built-in the bone plate 100 forming a unitary device with the bone plate 100. The washers 130 can provide a clearance for the physis of the bone and reduce contact with the periosteum of the bone.

In another aspect, and referring to FIGS. 3 and 3A, a bone plate 100 having an intermediate portion 119 in the form of an arch or hump, rather than an offset ramp, can be used depending on the anatomical contour of the specific patient or long bone. The intermediate portion 119 avoids placing bearing load on the physis of the bone or injuring the physis during the correction period, when the bone plate 100 is implanted in a pediatric patient for correcting a non-symmetric growth or other unequal bone growth or deformity. In other respects, the bone plate of FIGS. 3 and 3A is similar to bone plates of FIGS. 1-2.

The profile 116 of ramped bone plate 100 of FIG. 2 can match the anatomical features of the proximal tibia 90 before the bone fasteners are implanted through the bone plate 100. Further, the ramped profile 116 allows parallel placement of bone fasteners 150 through the holes 102, 104 of the bone plate 100, as shown in FIG. 8. Gradual angulation of the bone fasteners 150 relative to the bone plate 100 occurs over a longer period of time before reaching the maximum angulation of the growth control device. The extended period to maximum angulation can reduce the risk of bone fastener fracture, which can be greater when maximum angulation of the bone fastener 150 is reached such that the growth control device of the bone plate 100 and the bone fasteners 150 becomes substantially rigid while bone growth continues.

The combination of the stepped profile 116 and other features of the bone plate 100 of FIG. 2 with the ability of the bone fasteners 150 to angulate relative to an axis C perpendicular to the bone plate within a cone of angulation of an angle β can provide deformity correction during the physis growth period without closing the physis or completely preventing growth until maximum angulation is reached.

Various devices can be used for implanting the bone plate 100 and the bone fasteners 150, for interoperative manipulation of the bone plate 100 and for bone plate extraction. Referring to FIGS. 4, 4A, 4B and 5, a holding device 200 for the bone plate 100 in the form of forceps is illustrated. The holding device 200 has scissor-like gripping handles 216, first and second arms 212, 214 pivotably coupled with a pivot pin 210, and first and second legs (forceps tips) 202, 204 configured for holding the bone plate 100 from one end, and capturing a guide wire 300 that can pass through the corresponding end opening 122 of the bone plate 100. The distal ends of the forceps legs 202, 204 define a split curved groove or slot 230, in the form of a pair of slots 230, between corresponding upper and lower surfaces 232, 234. A pair of male notches or press pins 240 extend from the lower surface 234 substantially perpendicularly to the lower surface 234 and up to or stopping just short of the upper surface 232 of the slot 230. The split slot 230 is shaped to receive either end of the bone plate 100, such that the pins 240 engage the side notches 110 of the bone plate 100. The pins 240 can secure the bone plate 100 to the holding device 200 and prevent unintentional shifting of the bone plate 100 during tightening of the bone fasteners 150. The distal ends of the legs 202, 204 also define a split guiding bore 242 for receiving the guide wire 300 that passes through the end hole 112 of the bone plate 100 and between the legs 202, 204 of the forceps when the bone plate 100 is held in the slot 230 of the forceps 200, as shown in FIGS. 4A and 4B. The first and second legs 202, 204 of the holding device 200 can be contoured and cooperate with the spilt guiding bore 242 to provide an integrated guide for the guide wire 300 along the length of the legs 402, 404, as shown in FIG. 4A.

Referring to FIGS. 6 and 7, a targeting device 400 can be used for guiding the angulating bone fasteners 150 through the bone plate 100. The targeting device 400 can include a support bar or plate 406 having openings for receiving a support post 404 along an axis A and a tubular or cannulated drill guide 402 along an axis B at an angle a of about 16 degrees relative to the axis A, corresponding to a cone of maximum angulation of 32 degrees. The drill guide 402 can include a proximal end with an engagement formation for driver-assisted placement. The support post 402 can have a threaded distal end 408 threadably engaging the threaded third hole 106 of the bone plate 100. The extractor 350 illustrated in FIGS. 19 and 19A can be used as the support post 402. The targeting device 400 can be used with the holding device as shown in FIG. 7.

The growth control device can be provided in the form of a surgical kit including a plurality of bone plates 100 of different sizes and geometries with an arched intermediate portions 119 or a ramped intermediate portion 118, a holding device 200, a targeting device 400 with different size drill guides 402, a plate extractor 350, various guide wires 300 and drill bits and other instruments, such as an impact trocar, a ratcheting wrench, a torque driver, and the like.

Figure 10:
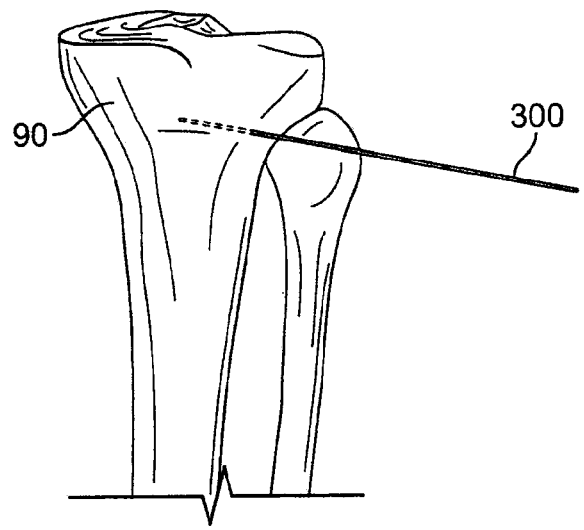
Figure 11:
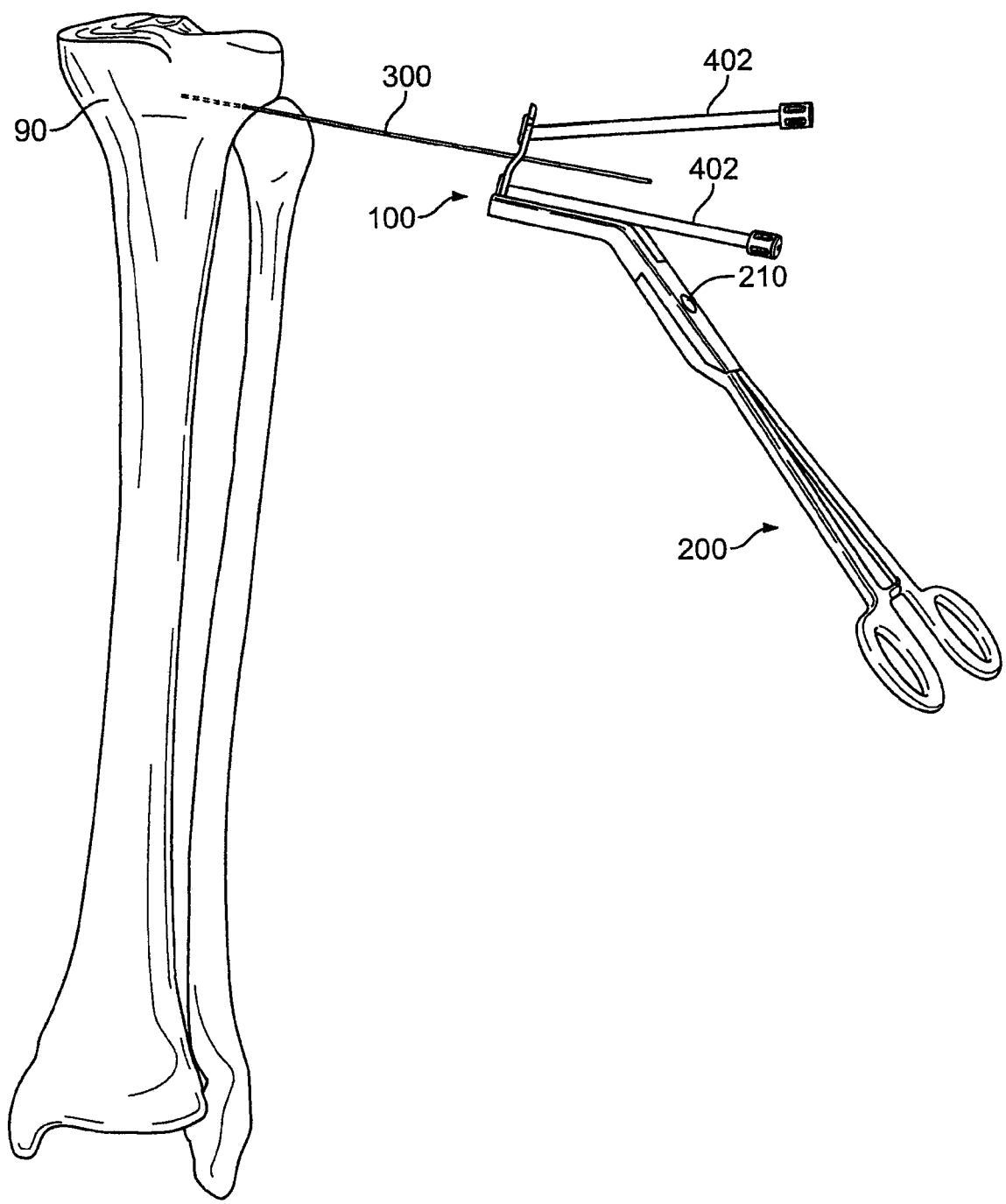
Figure 12:
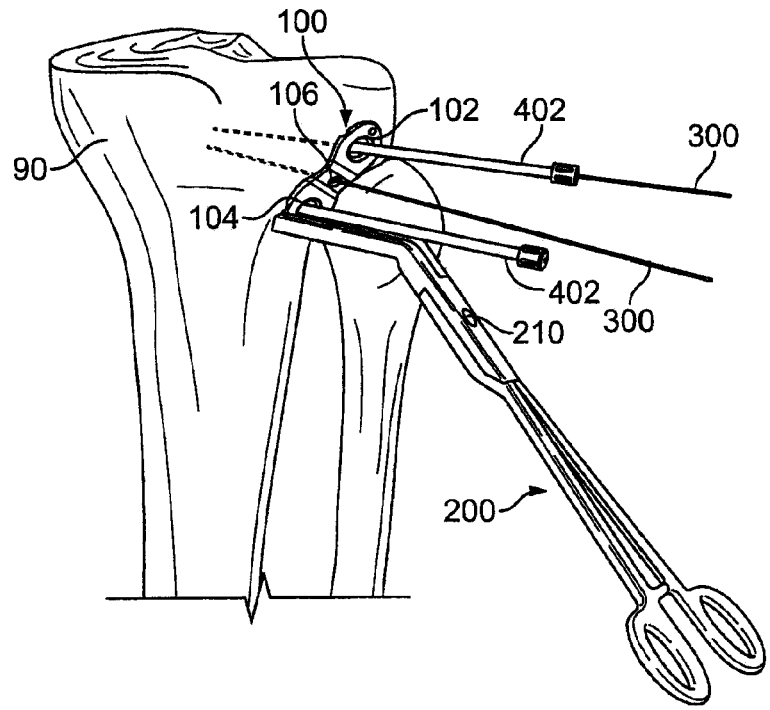

Referring to FIGS. 10-18, an exemplary surgical procedure for implanting the growth control device is illustrated. Referring to FIG. 10, a guide wire 300 can be inserted in the physis (growth plate) of the tibia 90. The bone plate 100, as held by the holding device 200 and with proximal and distal drill guides 402 engaging the corresponding first and second holes 102, 104 of the bone plate 100, can be passed over the guide wire 300, such that the guide wire 300 passes through the third hole 106 of the bone plate, as shown in FIGS. 11 and 12. Alternatively, if placement of a guide wire 300 into the physis is to be avoided, the guide wire 300 can inserted proximally or distally off the physis and received through the corresponding proximal or distal end hole 112 of the bone plate 100, as shown in FIG. 4A.

Figure 13:
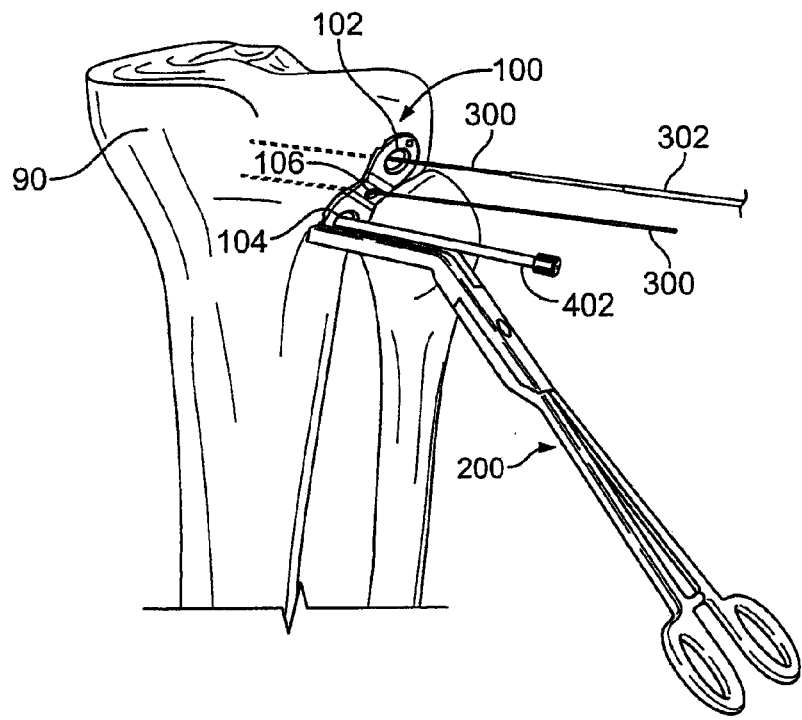
Figure 14:
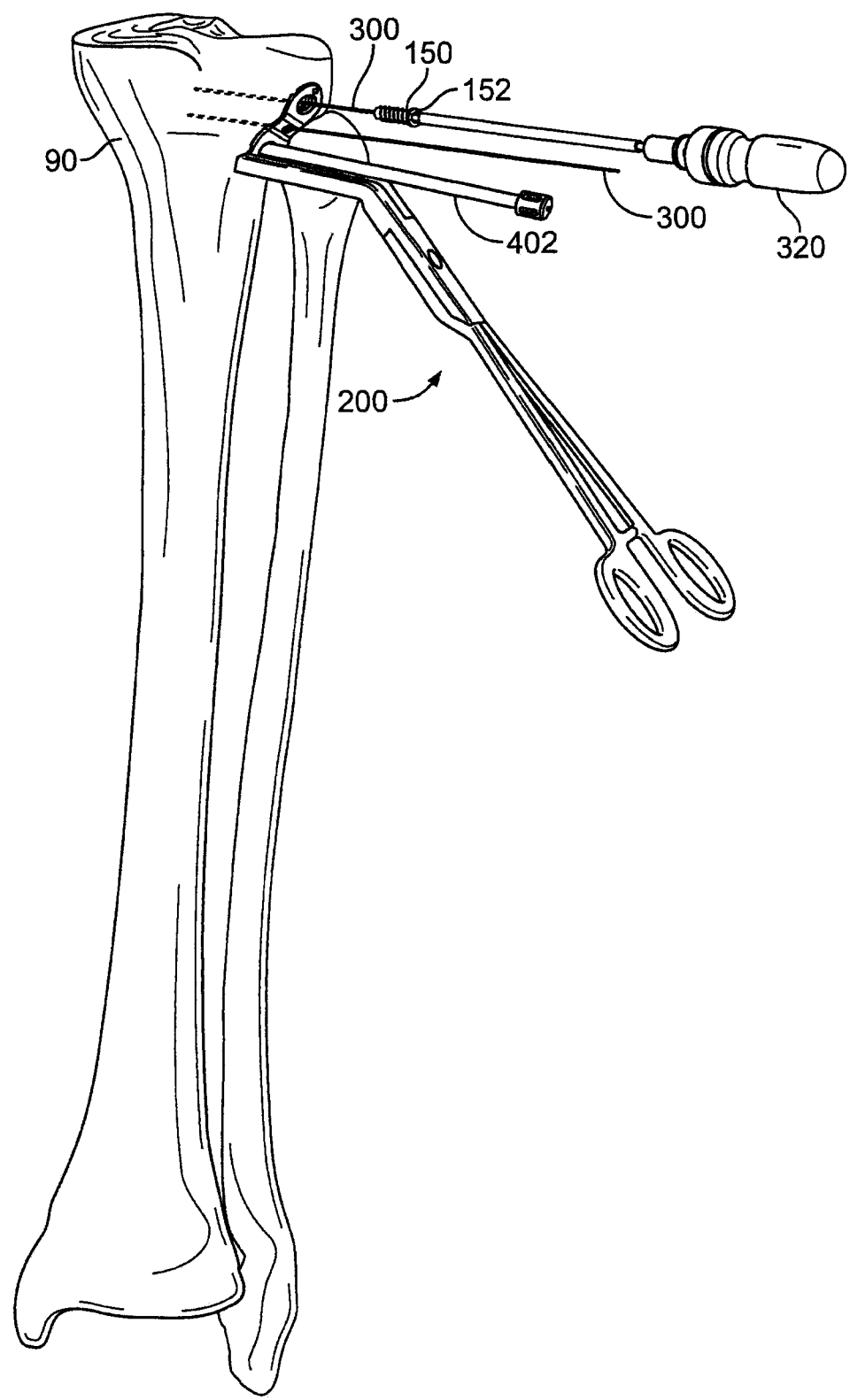

Another guide wire 300 is inserted into the proximal drill guide 402, as shown in FIG. 12, and the bone is drilled with a cannulated drill bit 302 placed over the proximal guide wire 300, as shown in FIG. 13. An appropriately sized bone fastener 150 can be selected and passed over the guide wire 300 using a driver 320 engaging the head 152 of the bone fastener 150, as shown in FIG. 14.

Figure 15:
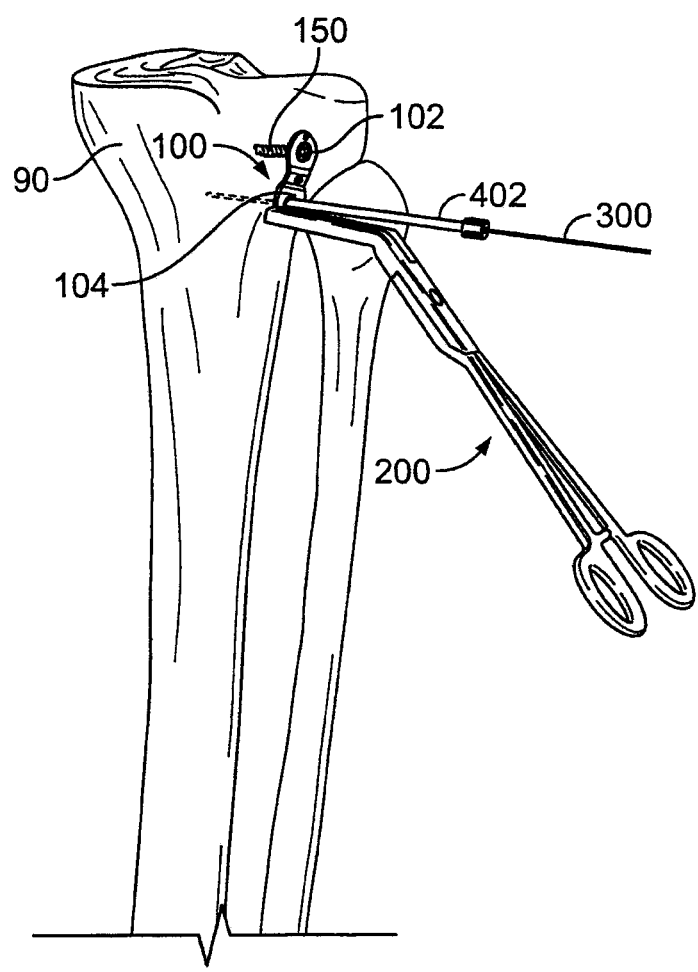
Figure 16:
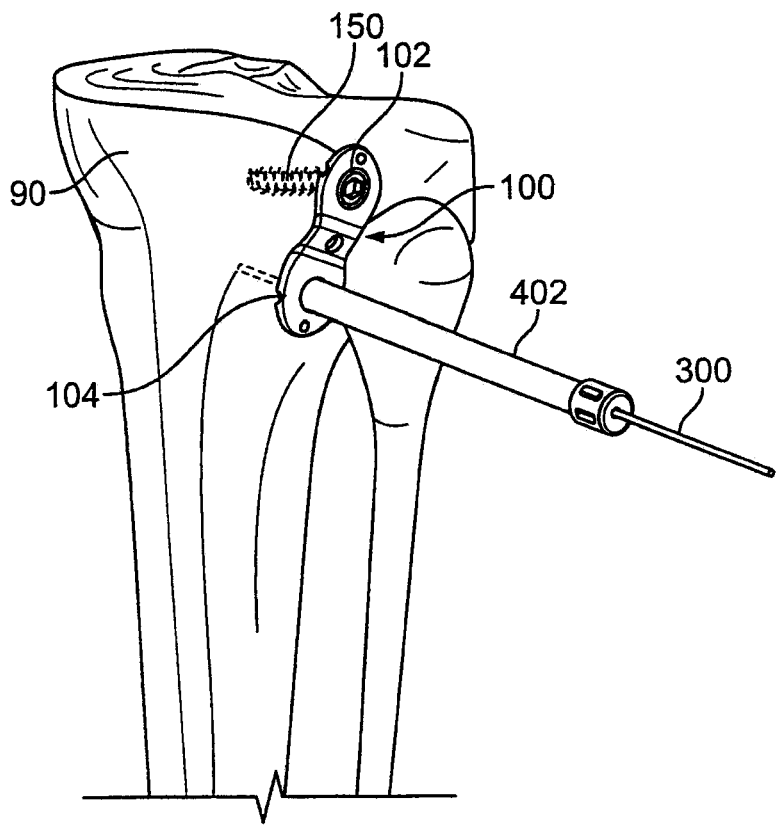
Figure 17:
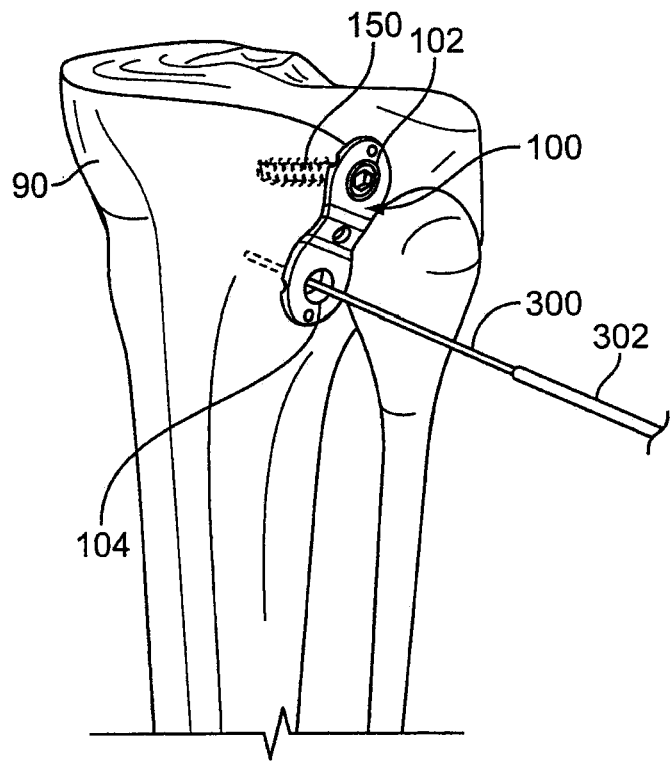

The procedure can be repeated for the distal bone fastener 150. A distal guide wire 300 can inserted through the distal drill guide 402, as shown in FIG. 15, and the holding device 200 can be removed, as shown in FIG. 16. A drill hole can be prepared for the distal bone fastener 150 with a drill bit 302 over the distal guide wire 300, as shown in FIG. 17, and the distal bone fastener 150 can be passed over the distal guide wire 300 and seated through the bone plate 100 into the tibia 90 with a driver 320, as shown in FIG. 18.

Although the implantation procedure is illustrated for the tibia, a bone plate 100 can be similarly placed on the femur, as shown in FIG. 8. As can be seen from FIG. 8, the initial placement of the bone fasteners 150 in each bone plate 100 can be such that the bone fasteners are substantially parallel or have a minimum amount of angulation to reduce the risk of breakage, as discussed above. The arched or stepped geometry of the bone plate 100 permits minimal contact with the lateral physis, as shown in FIG. 8, and can reduce the risk of pressure necrosis.

Referring to FIGS. 19, and 19A, the bone plate 100 can be removed with the extractor 350 after the bone fasteners 150 have been unscrewed and removed with a driver 320. The distal end 352 of the extractor 350 can include threads 354 engageable to the threaded inner surface 107 of the central hole 106 of the bone plate 100 for capturing and removing the bone plate 100. The distal end 352 of the extractor 150 can have a cutting flute 356 for passing through fibrous soft tissue and a curved tip 358 defining a non-invasive radius for avoiding accidental damage to the physis.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A growth control device comprising:
a bone plate having a stepped profile defined by a first level, a second level and an intermediate ramp connecting the first and second levels, each of the first level, the second level, and the intermediate ramp comprising a single threaded hole and collectively defining a longitudinal axis of the bone plate, the intermediate ramp being angled relative to the first level and the second level such that the first and second levels are vertically displaced from one another in separate first and second planes extending through and parallel to the respective first and second levels, the first and second planes being substantially parallel to one another, the first level including a first threaded hole for receiving a first bone fastener, and the second level including a second threaded hole for receiving a second bone fastener, wherein the bone plate includes a third threaded hole through the intermediate ramp, each of the first threaded hole, the second threaded hole, and the third threaded hole defining a centerpoint located along a single axis.

2. The growth control device of claim 1, wherein the bone plate is a monolithic component, further comprising first and second washers unitarily integrated with the bone plate and surrounding the first and second threaded holes on a bone engaging surface of the bone plate.

3. The growth control device of claim 2, wherein the first and second washers include a lower surface spaced apart from the bone engaging surface of the bone plate.

4. The growth control device of claim 3, wherein the first and second threaded holes define a substantially spherical surface in cross-section.

5. The growth control device of claim 4, wherein the first and second fasteners are capable of angulating within a cone of maximum angulation of an angle of about 32 degrees relative to an axis of the first or second threaded holes, the axis being perpendicular to the bone plate.

6. The growth control device of claim 1, further comprising first and second bone fasteners, each bone fastener having a substantially spherical head and capable of angulating relative to the bone plate when received through the corresponding first or second threaded holes of the bone plate.

7. The growth control device of claim 1, further comprising a proximal pair of side female notches, a distal pair of side female notches, a proximal guide hole and a distal guide hole.

8. The growth control device of claim 7, wherein the proximal pair and the distal pair of side female notches are formed in an outer perimeter sidewall of the bone plate.

9. The growth control device of claim 1, wherein the first and second planes are parallel to one another.

10. The growth control device of claim 1, wherein the first and second levels have a first width and the intermediate ramp has a second width, the second width being smaller than the first width.

11. The growth control device of claim 1, wherein the single axis is in alignment with the longitudinal axis of the bone plate.

12. A growth control device comprising:
a monolithic bone plate having a stepped profile defined by a first level, a second level and an intermediate ramp connecting the first and second levels, each of the first level, the second level, and the intermediate ramp comprising a single threaded hole, the intermediate ramp being angled relative to the first level and the second level such that the first and second levels are vertically displaced from one another in separate first and second planes extending through and parallel to the respective first and second levels, the first and second planes being parallel to one another, the first level including a first threaded hole for receiving a first bone fastener, the second level including a second threaded hole for receiving a second bone fastener, the bone plate including a proximal pair of side female notches, a distal pair of side female notches, a proximal guide hole and a distal guide hole, and the bone plate defining first and second washers unitarily integrated with the bone plate and surrounding the first and second threaded holes on a bone engaging surface of the bone plate.

13. The growth control device of claim 12, wherein the bone plate includes a third threaded hole through the intermediate ramp each of the first threaded hole, the second threaded hole, and the third threaded hole defining a centerpoint located along a single axis.

14. The growth control device of claim 12, wherein the first and second washers each include a lower surface spaced apart from the bone engaging surface of the bone plate.

15. The growth control device of claim 12, further comprising first and second bone fasteners, each bone fastener having a substantially spherical head and capable of angulating within a cone of maximum angulation of an angle of about 32 degrees relative to an axis perpendicular to the bone plate when received through the corresponding first or second threaded holes of the bone plate, wherein the first and second threaded holes define a substantially spherical surface in cross-section.

16. The growth control device of claim 12, wherein the proximal pair and the distal pair of side female notches are formed in an outer perimeter of the bone plate; and wherein the first and second levels have a first width and the intermediate ramp has a second width, the second width being smaller than the first width.

17. A growth control device comprising:
a plurality of bone plates of different sizes, each bone plate having first and second threaded holes and an intermediate portion between the first and second holes, the intermediate portion having a third threaded hole, each of the first threaded hole, the second threaded hole, and the third threaded hole defining a centerpoint located along a single axis, the plurality of bone plates including at least one stepped bone plate having first and second levels connected by the intermediate portion in the form of an angled ramp such that the first and second levels are vertically displaced from one another in separate first and second planes extending through and parallel to the respective first and second levels, the first and second planes being parallel to one another and each of the first level, the second level, and the intermediate ramp comprising a single threaded hole, and at least one arched bone plate having the intermediate portion in the form of a curved arch.

18. The growth control device of claim 17, wherein each of the bone plates is a monolithic component and includes first and second washers unitarily attached to the bone plate and surrounding the first and second threaded holes on a bone engaging surface of the bone plate.

19. The growth control device of claim 18, further comprising a plurality of threaded bone fasteners, each bone fastener having a head, the head angulatably received within one of the first or second threaded holes, such that a longitudinal axis of the bone fastener can angulate within a cone of maximum angulation of an angle of about 32 degrees relative to an axis perpendicular to the bone plate.

20. The growth control device of claim 19, wherein the head includes a substantially spherical head and the first and second threaded holes define a substantially spherical surface in cross-section.

21. The growth control device of claim 17, wherein each bone plate includes a proximal pair of side female notches, a distal pair of side female notches, a proximal guide hole and a distal guide hole.

22. The growth control device of claim 17, wherein the at least one stepped bone plate includes the first and second levels having a first width and the angled ramp having a second width, the second width being smaller than the first width.

* * * * *